(12) United States Patent
Matin et al.

(10) Patent No.: US 7,687,474 B2
(45) Date of Patent: Mar. 30, 2010

(54) NITROREDUCTASE ENZYMES

(75) Inventors: A. C. Matin, Stanford, CA (US); Yoram Barak, Menlo Park, CA (US); Susan V. Lynch, San Francisco, CA (US); David F. Ackerley, Wellington (NZ); Stephen H. Thorne, Palo Alto, CA (US); Christopher H. Contag, Stanford, CA (US); Jianghong Rao, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/643,628

(22) Filed: Dec. 20, 2006

(65) Prior Publication Data

US 2007/0254852 A1    Nov. 1, 2007

Related U.S. Application Data

(60) Provisional application No. 60/752,517, filed on Dec. 20, 2005.

(51) Int. Cl.
*A61K 48/00*    (2006.01)
*C12N 5/00*    (2006.01)

(52) U.S. Cl. .................................. 514/44; 435/320.1

(58) Field of Classification Search ................. 514/44
See application file for complete search history.

(56) References Cited

OTHER PUBLICATIONS

Wu et al, (Archives of Biochemistry and Biophysics, 385(1): 203-208, 2001.*
Theys et al, (Current Gene Therapy, 3: 207-221, 2003.*
Ackerley et al., "Chromate-reducing properties of soluble flavoproteins from *Pseudomonas putida* and *Escherichia coli*", Appl. Environ. Microbiol., 2004, 70(2):873-882.
Ackerley et al., "Mechanism of chromate reduction by the *Escherichia coli* protein NfsA, and the role of different chromate reductases in minimizing oxidative stress during chromate reduction", Environ Microbiol., 2004, 6(8):851-860.
Barak et al., Poster A33: Improvement of a Novel Enzyme, Using Directed Evolution, for Reductive Cancer Chemotherapy, European Organization for Research and Treatment of Cancer "Molecular targets and Cancer Therapeutics" Conference, Philadelphia, PA, Nov. 14-18, 2005.
Pawelek et al., "Tumor-targeted *Salmonella* as a novel anticancer vector", Cancer Research, 1997, 57 (20):4537-4544.

* cited by examiner

*Primary Examiner*—Anne-Marie Falk
*Assistant Examiner*—Magdalene K Sgagias
(74) *Attorney, Agent, or Firm*—Bozicevic, Field & Francis LLP; Pamela J. Sherwood

(57) ABSTRACT

Compositions and methods are provided for the treatment of cancer.

11 Claims, 11 Drawing Sheets

B

B.

HeLa cells + CNOB    HeLa cells + SL7838(GFP)-Y6 + CNOB

SEQUENCE LISTING

```
<160> NUMBER OF SEQ ID NOS: 1

<210> SEQ ID NO 1
<211> LENGTH: 188
<212> TYPE: PRT
<213> ORGANISM: E. coli

<400> SEQUENCE: 1

Met Ser Glu Lys Leu Gln Val Val Thr Leu Leu Gly Ser Leu Arg Lys
 1               5                  10                  15

Gly Ser Phe Asn Gly Met Val Ala Arg Thr Leu Pro Lys Ile Ala Pro
            20                  25                  30

Ala Ser Met Glu Val Asn Ala Leu Pro Ser Ile Ala Asp Ile Pro Leu
        35                  40                  45

Tyr Asp Ala Asp Val Gln Gln Glu Asp Gly Phe Pro Ala Thr Val Glu
    50                  55                  60

Ala Leu Ala Glu Gln Ile Arg Gln Ala Asp Gly Val Val Ile Val Thr
65                  70                  75                  80

Pro Glu Tyr Asn Tyr Ser Val Pro Gly Gly Leu Lys Asn Ala Ile Asp
                85                  90                  95

Trp Leu Ser Arg Leu Pro Asp Gln Pro Leu Ala Gly Lys Pro Val Leu
            100                 105                 110

Ile Gln Thr Ser Ser Met Gly Val Ile Gly Gly Ala Arg Cys Gln Tyr
        115                 120                 125

His Leu Arg Gln Ile Leu Val Phe Leu Asp Ala Met Val Met Asn Lys
    130                 135                 140

Pro Glu Phe Met Gly Gly Val Ile Gln Asn Lys Val Asp Pro Gln Thr
145                 150                 155                 160

Gly Glu Val Ile Asp Gln Ser Thr Leu Asp His Leu Thr Gly Gln Leu
                165                 170                 175

Thr Ala Phe Gly Glu Phe Ile Gln Arg Val Lys Ile
            180                 185
```

NITROREDUCTASE ENZYMES

CROSS-REFERENCE TO RELATED APPLICATIONS

This application claims the benefit of U.S. Provisional Application No. 60/752,517, filed Dec. 20, 2005, which application is incorporated herein by reference.

FEDERALLY-SPONSORED RESEARCH OR DEVELOPMENT

This invention was made with Government support under contract DE-FG02-03ER63627 awarded by the U.S. Department of Energy and contracts CA092862 and CA049605 awarded by the NIH. The Government has certain rights in this invention.

BACKGROUND OF THE INVENTION

Neoplasia is a process that occurs in cancer, by which the normal controlling mechanisms that regulate cell growth and differentiation are impaired, resulting in progressive growth. This impairment of control mechanisms allows a tumor to enlarge and occupy spaces in vital areas of the body. If the tumor invades surrounding tissue and is transported to distant sites it will likely result in death of the individual.

The desired goal of cancer therapy is to kill cancer cells preferentially, without having a deleterious effect on normal cells. Several methods have been used in an attempt to reach this goal, including surgery, radiation therapy, and chemotherapy.

Local treatments, such as radiation therapy and surgery, offer a way of reducing the tumor mass in regions of the body that are accessible through surgical techniques or high doses of radiation therapy. However, these treatments are not applicable to the destruction of widely disseminated or circulating tumor cells eventually found in most cancer patients. In order to combat the spread of tumor cells, systemic therapies are used.

The primary weapon against cancer is chemotherapy. However, chemotherapeutic agents are limited in their effectiveness for treating many cancer types, including many common solid tumors. This failure is in part due to the intrinsic or acquired drug resistance of many tumor cells. Another drawback to the use of chemotherapeutic agents is their severe side effects. These include bone marrow suppression, nausea, vomiting, hair loss, and ulcerations in the mouth.

Reductive prodrugs are compounds that are nontoxic in their native form, but produce a highly toxic species when reduced. These drugs kill by generating DNA adducts and can target both growing and non-growing tumor cells, which is advantageous since in human tumors, generally only a small fraction of cells are actively replicating at a given time. Reductive prodrug cancer chemotherapy with compounds such as MMC and CB 1954 owes its rationale to the fact that he concentration of the enzymes that reduce them, such as mammalian DT-diaphorase (NQO1) increases in tumor cells. This makes the tumor cells more potent reducers of these drugs, and therefore more susceptible to their killing effect. However, these enzymes are present also in normal mammalian cells, and while their activity is lower in such cells than in tumor cells, it is high enough to produce severe side effects.

One approach to preferentially killing pathological cells, most widely used for treating cancer, is to introduce a gene into the target cells that encodes an enzyme capable of converting a prodrug of relatively low toxicity into a potent cytotoxic drug. Systemic administration of the prodrug is then tolerated since it is only converted into the toxic derivative locally, for example in a tumor, by cells expressing the prodrug-converting enzyme. This approach is known as gene-directed enzyme prodrug therapy (GDEPT), or when the gene is delivered by means of a recombinant viral vector, virus-directed prodrug therapy (VDEPT) (McNeish et al, 1997). A class of enzymes that has been well studied in GDEPT is bacterial nitroreductases (NTRs), such as NfsA and NfsB from *Escherichia coli*. These enzymes can reduce several nitro substituted organic compounds.

An example of an enzyme/prodrug system is nitroreductase and the aziridinyl prodrug CB1954 (5-aziridinyl-2,4-dinitrobenzamide) (Knox et al 1988). CB1954 is a poor substrate for the human nitroreductase, and so GDEPT was conceived as a way of introducing a suitable nitroreductase, preferably with greater activity against CB1954, in order to sensitize targeted cells. The *E. coli* nitroreductase has been widely used for this purpose.

Targeted biological therapies hold tremendous potential for the treatment of cancers, yet their effective use has been limited by constraints on delivery and effective tumor targeting. There exists a need for a local therapy that provides for effective killing of tumor cells. The present invention addresses this need.

Relevant Literature

Pawelek et al. (1997) Cancer Research, Vol 57, Issue 20 4537-4544. European Organisation for Research and Treatment of Cancer "Molecular Targets and Cancer Therapeutics" Conference, Philadelphia, Pa. Nov. 14-18 2005. Poster A33: Improvement of a Novel Enzyme, Using Directed Evolution, for Reductive Cancer Chemotherapy, Barak et al. Ackerley et al. Environ Microbiol. August 2004;6(8):851-60, "Mechanism of chromate reduction by the *Escherichia coli* protein, NfsA, and the role of different chromate reductases in minimizing oxidative stress during chromate reduction". Ackerley et al. (2004) Appl Environ Microbiol. February;70 (2):873-82, "Chromate-reducing properties of soluble flavoproteins from Pseudomonas

SUMMARY OF THE INVENTION

Methods are provided for the treatment of cancer, through administration to a patient of prodrugs comprising an activatable nitro moiety, e.g. prodrugs in the dinitrobenzamide class; or quinone based prodrugs reduced to the semiquinol or hydro-quinone form, e.g. mytomicin C; and the activating *E. coli* enzyme NAD(P)H oxidoreductase ChrR (formerly called YieF). The ChrR enzyme may be used in a native form, or in improved forms having enhanced enzyme kinetics for reduction of quinones and nitro compounds. In some embodiments the enzyme is provided to a patient in the form of a nucleic acid, where the enzyme is expressed in situ. The nucleic acid is optionally localized to the site of the cancer by physical means, or through the use of regulatable vectors having selective expression at the site of cancer or in cancer cells.

In some embodiments the prodrug produces a detectable product upon reduction, e.g. a fluorescent compound. The production of the drug from the prodrug can thus be imaged in vitro or in vivo. The tracking of the delivery vehicle and the prodrug provides for methods of in vivo analysis of cancer therapy.

In some embodiments of the invention, vectors comprising nucleic acid sequences encoding ChrR are provided. Such vectors may provide for expression of the ChrR enzyme.

Vectors of interest include plasmids, viruses capable of expression in mammalian cells, bacterial cells, and the like. In one embodiment, the vector is provided in an attenuated strain of *Salmonella typhimurium*. These bacteria have been shown to target both the aerobic and anaerobic zones of tumors, and do not infect normal tissues. In another embodiment, the vector is provided as a virus particle. In another embodiment, the vector, which may be present in a bacterial cell or viral coat, is provided in a pharmaceutical formulation. In another embodiment, the ChrR enzyme is delivered to cells, including fusion proteins comprising active ChrR enzyme, such as fusions with an immunoglobulin.

Also provided are screening methods for the analysis of enzyme variants having enhanced nitroreductase activity, e.g. for screening of CHrR variants.

BRIEF DESCRIPTION OF THE DRAWINGS

These and other objects, features and many of the attendant advantages of the invention will be better understood upon a reading of the detailed description of the invention when considered in connection with the accompanying drawings which show as follows:

FIGS. 4A-4B. The effect of different durations of cell exposure on viability in the presence of NfsA or Y6 enzyme (50 µg ml$^{-1}$) and 15 µM MMC (A) or CB 1954 (B). The duration of the incubation periods were: 10, (■); 20, (■); 60, (■); 120, (■), or 180, (□) min.

DETAILED DESCRIPTION OF THE EMBODIMENTS

Figure 1:
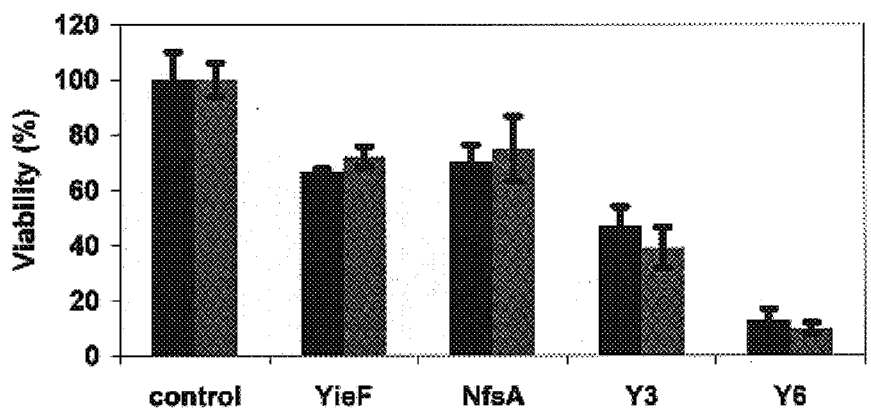
FIG. 1. The effect of wild type NfsA or YieF (now ChrR) or the evolved enzymes (50 µg ml$^{-1}$) in the presence of 15 µM MMC (■) or CB 1954 (■) on the viability of HeLa cells. 'Control' refers to incubation of the cells with the prodrug alone; other controls (incubation of cells alone or with just the enzyme) gave similar results.

The objects and advantages of the present invention are achieved by a method of treating malignancy in a patient; comprising administering prodrugs comprising an activatable nitro moiety or reduced quinones, e.g. prodrugs in the dinitrobenzamide class; and the activating enzyme ChrR. The ChrR enzyme may be used in a native form, or in improved forms having enhanced enzyme kinetics for nitroreductase activity. In some embodiments the enzyme is provided to a patient in the form of a nucleic acid, where the enzyme is expressed in situ. The nucleic acid is optionally localized to the site of the cancer by physical means, or through the use of regulatable vectors having selective expression at the site of cancer or in cancer cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

As used herein, a "target cell" is a tumor cell. Usually a target cell is a mammalian cell, preferably a human cell.

The term "gene" is well understood in the art and includes polynucleotides encoding a polypeptide. In addition to the polypeptide coding regions, a gene may includes non-coding regions including, but not limited to, introns, transcribed but untranslated segments, and regulatory elements upstream and downstream of the coding segments.

The terms "polypeptide", "peptide" and "protein" are used interchangeably to refer to polymers of amino acids of any length. These terms also include proteins that are post-translationally modified through reactions that include glycosylation, acetylation and phosphorylation.

As used herein, "cytotoxicity" is a term well understood in the art and refers to a state in which one or more of a cell's usual biochemical or biological functions are perturbed. These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, 3H-thymidine uptake, and plaque assays. The term "selective cytotoxicity", as used herein, refers to the cytotoxicity conferred by an enzyme in conjunction with a prodrug on a target cell, compared to the cytotoxicity conferred by the prodrug in the absence of the bacterial enzyme. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen or tumor reduction size using firefly tuciferase expressing tumor cells to allowing visualization in-situ of the target cells.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, rodents, primates, farm animals, sport animals, and pets.

An "effective amount" is an amount sufficient to effect beneficial or desired clinical results. An effective amount can be administered in one or more administrations. For purposes of this invention, an effective amount of an enzyme in conjunction with a prodrug is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment. "Palliating" a disease means that the extent and/or undesirable clinical manifestations of a disease state are lessened and/or time course of the progression is slowed or lengthened, as compared to not administering the methods of the present invention.

The term "prodrug" refers to a compound that is converted via one or more enzymatically catalyzed steps into an active compound that has an increased pharmacological activity relative to the prodrug. The term "drug" and "active drug" refer to the active moieties of a prodrug. After chemical modification by ChrR, the active drug acts therapeutically upon the targeted tumor cell. In another example, the prodrug is chemically modified by the activating enzyme, for example, by oxidation, reduction, phosphorylation, dephosphorylation, the addition of a moiety, or the like.

Prodrugs of interest for the methods of the invention comprise one or more nitro groups, which groups are acted upon by the enzyme ChrR to generate an active form of the drug. Examples of such prodrugs include those of the dinitrobenzamide and the quinone based classes. Such drugs include, without limitation, 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl]amino]-5,8-dihydroxyanthracene-9,10-dione (AQ4), the dinitrobenzamide mustard compound SN 23862 and related amide-substituted mustard SN 27217; nitroaniline-based alkylating agents as described in U.S. patent application 20050256191 (herein incorporated by reference for the teaching of such prodrugs); mitomycin C, 17-allylamino-17-demethoxygeldanamycin (17-MG), and the like.

As used herein, the terms "neoplastic cells", "neoplasia", "transformed", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

Cancer, as used herein, refers to hyperproliferative conditions. The term usually denotes malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Cancers include leukemias, lymphomas (Hodgkins and non-Hodgkins), sarcomas, melanomas, adenomas, carcinomas of solid tissue including breast cancer and pancreatic cancer, hypoxic tumors, squamous cell carcinomas of the mouth, throat, larynx, and lung, genitourinary cancers such as cervical and bladder cancer, hematopoietic cancers, head and neck cancers, and nervous system cancers, such as gliomas, astrocytomas, meningiomas, etc., benign lesions such as papillomas, and the like.

ChrR Polypeptides

For use in the subject methods, the native ChrR protein from *E. coli*; homologs from related bacteria; variants derived therefrom; or a combination thereof may be used. The sequence of native *E. coli* ChrR is as follows: (SEQ ID NO:1) MSEKLQVVTL LGSLRKGSFN GMVARTLPKI APAS-MEVNAL PSIADIPLYD ADVQQEDGF PATVEALAEQI RQADGVVIVT PEYNYSVPGG LKNAIDWLSR LPDQ-PLAGKP VLIQTSSMGV IGGARCQYHL RQILVFLDAM VMNKPEFMGG VIQNKVDPQT GEVIDQSTLD HLT- GQLTAFG EFIQRVKI. The sequence is available at Genbank, accession number DQ989184.

Homologs of ChrR are known in the art, e.g. from such bacterium as *Shigella boydii; Salmonella enterica; Shigella flexneri; Salmonella typhimurium; Pseudomonas aeruginosa; Streptomyces coelicolor; Bacillus subtilis; Lactococcus lactis*, etc. Such homologs usually have at least about 35% amino acid identity with SEQ ID NO:1, more usually at least about 45% sequence identity; and may be at least about 80% sequence identity; at least about 85%, at least about 90%, or more. In some embodiments a fragment of a ChrR peptide may be utilized. Peptides of interest include fragments of at least about 50 contiguous amino acids, more usually at least about 100 contiguous amino acids, and may comprise 150 or more amino acids, up to the full length polypeptide. Fragments also included truncated forms of the polypeptide, where deletions may be from about 1 to about 5, to about 10, to about 15, to about 20, to about 25 amino acids, and may extend from residue 1 through 25 at either terminus of the polypeptide, comprising deletions of any length within the region; or may be at an internal location.

The sequence of the ChrR polypeptide may be altered in various ways known in the art to generate changes in sequence. The polypeptide will usually be substantially similar to the sequences provided herein, i.e. will differ by at least one amino acid, and may differ by at least two but not more than about ten amino acids. Where changes are introduced by shuffling or any other means of random mutation method, the amino acid differences may be greater. The sequence changes may be substitutions, insertions or deletions. Scanning mutations that systematically introduce alanine, or other residues, may be used to determine key amino acids.

In one embodiment of the invention, the polypeptide comprises an amino acid substitution at the position corresponding to amino acid 128 of SEQ ID NO:1. It will be understood by one of skill in the art that the corresponding amino acid can be determined in homologous polypeptides by alignment of the two sequences using conventional algorithms, e.g. BLASTN, CLUSTALW, and the like.

The native *E. coli* polypeptide contains a tyrosine at position 128, and substitutions of interest include an amino acid other than tyrosine at position 128. Substitutions of interest at this position include asn (asparagine), and amino acids that are conservative with respect to asn, including gin (glutamine). Other residues that commonly substitute for asparagine in homologous proteins include asp (aspartic acid); his (histidine); ser (serine); gly (glycine); lys (lysine); arg (arginine); glu (glutamine) and thr (threonine). A polypeptide with a tyr128asn substitution may be referred to as ChrR21.

In other embodiments of the invention, the polypeptide comprising an amino acid substitution at the position corresponding to amino acid 128 of SEQ ID NO:1 further comprises an amino acid substitution at the position corresponding to amino acid 150 of SEQ ID NO:1, where the substituted amino acid is other than glycine. Substitutions of interest include serine and amino acids that are conservative with respect to serine, including threonine, cysteine, and the like.

In other embodiments of the invention, the polypeptide comprising an amino acid substitution at the position corresponding to amino acid 128 of SEQ ID NO:1 may further comprise an amino acid substitution at the position corresponding to amino acid 154 of SEQ ID NO:1, where the substituted amino acid is other than asparagine. Substitutions of interest include threonine and amino acids that are conservative with respect to threonine, including serine, cysteine, and the like.

Modifications of interest that do not alter primary sequence, and which may be applied to the native sequence or to derivatives thereof include chemical derivatization of polypeptides, e.g., pegylation, acylation, acetylation, carboxylation, etc. Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art, or expressed from a polynucleotide construct. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The subject peptides may be prepared by in vitro synthesis, using conventional methods as known in the art, or expressed from a pqlynucleotide construct. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some embodiments of the invention, the ChrR enzyme is selected for enhanced cytotoxic activity in the presence of the nitro derivative or quinone based prodrugs such as CB 1954 and mitomycin C. In such screening assays, directed or non-directed mutations are introduced into the enzyme. Directed mutations include the use of various methods known in the art to introduce sequences into a targeted position, where the introduced sequences can comprise random sequences or can encode specific amino acids of interest. Non-directed mutations include the growth of cells in various mutagens, the use of error-prone PCR, and the like.

Nitroreductase enzymes can be screened indirectly for Cr(VI) reduction. For example the colorimetric diphenyl carbazide assay of Greenberg et al (Greenberg, A. E., J. J. Connors, D. Jenkins, and M. A. Franson (ed.). 1981. Standard methods for the examination of water and wastewater, 15th ed., p.187-190. American Public Health Association, Washington, D.C.) has been used. Alternatively the end product of chromate reduction can be determined using the X-ray absorption near-edge structure (XANES) spectrum. In this method, Cr(VI) and Cr(III) can be distinguished by the pronounced pre edge feature of the former. The fraction of Cr(VI) was calculated by dividing the height of the Cr(VI) pre edge peak by the total absorption; that of Cr(III) was calculated from the difference between the amount of chromium represented by the pre edge peak and the total absorption jump.

The enzymes thus screened, or new variants, may be screened in a direct method of detecting enhanced nitroreductase activity. Substrates of interest include those that produce a detectable product upon reduction, e.g. 6-chloro-9-nitro-5-oxo-5H-benzo[a]phenoxazine (CNOB), which is an analogue of CB 1954 in the nitro group being reduced. Reduction of CNOB generates a highly fluorescent compound (aminophenoxazine) and thus permits rapid and direct screening for prodrug-reducing activity. CNOB can also act as prodrug with the same efficiency as CB1954 in in vitro cytotoxicity assays. As its cytotoxic product is fluorescent, it can be monitored in vivo. The tracking of both the delivery vehicle and the prodrug provides for unique assays in vivo for cancer gene therapy.

Thus, in one embodiment of the invention, an assay is provided wherein the prodrug CNOB is administered to a patient or animal. The fluorescent product is used to monitor the efficacy of activation in an in vivo environment. In some embodiments, a laboratory animal is used in such a method, e.g. mouse, rat, rabbit, etc. In other embodiments, a human patient is treated in such a method.

ChrR Nucleic Acids

The invention includes nucleic acids that encode the sequence set forth in SEQ ID NO:1 and variants or homologs thereof, particularly variants or homologs encoding an amino acid substitution at positions 128; 150 and/or 154; nucleic acids that hybridize under stringent conditions, particularly conditions of high stringency, to the sequences that encode the sequence set forth in SEQ ID NO:1; and fragments and derivatives thereof. For example, the native sequence encoding SEQ ID NO:1 may be accessed at GenBank, accession no. NC_000913.2. One of skill in the art will readily appreciate that the redundancy of the genetic code allows many silent changes to be made in the coding sequence. Other nucleic acid compositions contemplated by and within the scope of the present invention will be readily apparent to one of ordinary skill in the art when provided with the disclosure here.

The nucleic acids of the invention include nucleic acids having sequence similarity or sequence identity to sequences that encode the sequence set forth in SEQ ID NO:1. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, homologs, genetically altered versions of the gene, etc., bind to sequences that encode the sequence set forth in SEQ ID NO:1 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The invention also encompasses homologs corresponding to the sequences that encode the sequence set forth in SEQ ID NO:1, where the source of homologous genes can be any species, particularly bacterial species, e.g. gram negative bacteria, particularly *Enterobacteriaceae*.

A genomic sequence of interest comprises the nucleic acid present between the initiation codon and the stop codon. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt selected from the nucleic acid sequence.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression Constructs

In the present methods, ChrR may be produced by recombinant methods. The DNA encoding ChrR polypeptide may be obtained from any library prepared from suitable cells, prepared from various sources according to the desired ChrR. The ChrR polypeptide-encoding gene may also be obtained by oligonucleotide synthesis. As described above, there are many ChrR-related polypeptides and genetic sequences known in the art. Libraries may be screened with probes (such as antibodies to the ChrR polypeptide, or oligonucleotides of about 20-80 bases) designed to identify the gene of interest or the protein encoded by it. Screening the cDNA or genomic library with the selected probe may be conducted using standard procedures as described in Sambrook et al, Molecular Cloning: A Laboratory Manual (New York: Cold Spring Harbor Laboratory Press, 1989). An alternative means to isolate the gene encoding ChrR polypeptide is to use PCR methodology.

The nucleic acid encoding a ChrR polypeptide is inserted into a replicable vector for expression. Many such vectors are available. The vector components generally include, but are not limited to, one or more of the following: an origin of replication, one or more marker genes, an enhancer element, a promoter, and a transcription termination sequence. In some embodiments, for example in the utilization of bacterial delivery agents such as Salmonella, the chrR gene is integrated into the host cell chromosome.

ChrR polypeptides may be produced recombinantly not only directly, but also as a fusion polypeptide with a heterologous polypeptide, e.g. a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to the ChrR coding sequence. Promoters are untranslated sequences located upstream (5') to the start codon of a structural gene (generally within about 100 to 1000 bp) that control the transcription n of particular nucleic acid sequence to which they are operably linked. In bacterial cells, the region controlling overall regulation can be referred to as the operator. Promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native ChrR polypeptide promoter sequence and many heterologous promoters may be used to direct expression of a ChrR polypeptide. However, heterologous promoters are preferred, as they generally permit greater transcription and higher yields.

Promoters suitable for use with prokaryotic hosts include the β-lactamase and lactose promoter systems, alkaline phosphatase, a tryptophan (trp) promoter system, hybrid promoters such as the tac promoter, and starvation promoters (Matin, A. (1994) Recombinant DNA Technology II, Annals of New York Academy of Sciences, 722:277-291). However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes, e.g. for use with viral expression systems. Examples of suitable promoting sequences include promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter. Small RNAs may be used for enhancing translation.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonads* such as *P. aeruginosa*, and *Streptomyces*. These examples are illustrative rather than limiting.

In some embodiments of the invention, the expression vector is a plasmid or bacteriophage vector suitable for use in Salmonella typhimurium, and the ChrR polypeptide is provided to a patient through expression by an attenuated *S.*

*typhimurium* cell administered to the patient. The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures. Replicating plasmids can be identified using standard assays including the standard replication assay of Ustav and Stenlund (1991).

The present invention also provides a host cell transfected with the isolated polynucleotide or vector comprising such a polynucleotide of the present invention. The host cell may be a mammalian cell, e.g. a patient cell transfected with a viral vector, or may be a bacterial cell, e.g. an attenuated *S. typhimurium* cell.

Expression vectors of interest include any DNA or RNA vector used in Viral Directed Enzyme Prodrug Therapy (VDEPT) or Gene Directed Enzyme Prodrug Therapy (GDEPT) therapies. Integrating vectors of interest include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication on the target cells. In such cases, the replication-defective viral genome can be packaged by a helper virus in accordance with conventional techniques. Generally, any retrovirus meeting the above criteria of infectivity and capability of functional gene transfer can be employed in the practice of the invention. Lentiviral vectors are especially preferred. Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm.

Examples of vector systems include vectors based on the Molony murine leukaemia virus (Ram et al., Cancer Research (1993) 53; 83-88; Dalton and Triesman, Cell (1992) 68; 597-612). These vectors contain the murine leukaemia virus (MLV) enhancer cloned upstream at a ⊖-globin minimal promoter. The β-globin 5' untranslated region up to the initiation ATG is supplied to direct efficient translation of the cloned protein. The initiator ATG straddles an NcoI restriction site and thus can be used to clone a protein coding sequence into the vector. This vector further contains a polylinker to facilitate cloning, followed by the .beta.-globin 5' untranslated region and polyadenylation sites. The MLV enhancer is of particular use since it is a strong enhancer and is active in most murine and human cells.

Suitable viral vectors further include those which are based upon a retrovirus. Such vectors are widely available in the art. Huber et al., (Proc. Natl. Acad. Sci. USA (1991) 38, 8039) report the use of amphotropic retroviruses for the transformation of hepatoma, breast, colon or skin cells. Culver et al (Science (1992) 256; 1550-1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described above for MLV.

Englehardt et al (Nature Genetics (1993) 4; 27-34) describes the use of adenovirus based vectors in the delivery of the cystic fibrosis transmembrane conductance product (CFTR) into cells, and such adenovirus based vectors may also be used. Vectors utilizing the adenovirus promoter and other control sequences may be of use in delivering a system according to the invention to cells. Adenovirus vectors are well known to those skilled in the art and have been used to deliver genes to numerous cell types, including airway epithelium, skeletal muscle, liver, brain and skin (Hitt et al, 1997; Anderson, 1998).

Another vector is the adeno-associated (MV) vector. MV vectors are well known to those skilled in the art and have been used to stably transduce human T-lymphocytes, fibroblasts, nasal polyp, skeletal muscle, brain, erythroid and haematopoietic stem cells for gene therapy applications (Philip et al., 1994; Russell et al., 1994; Flotte et al., 1993; Walsh et al., 1994; Miller et al., 1994; Emerson, 1996). International Patent Application WO 91/18088 describes specific MV based vectors.

Other episomal vectors include transient non-replicating episomal vectors and self-replicating episomal vectors with functions derived from viral origins of replication such as those from EBV, human papovavirus (BK) and BPV-1. Such integrating and episomal vectors are well known to those skilled in the art and are fully described in the body of literature well known to those skilled in the art. In particular, suitable episomal vectors are described in WO98/07876.

Numerous techniques are known and are useful according to the invention for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi, 1984; Keown et al., 1990; Weir, 1999; Nishikawa and Huang, 2001).

A vector of the invention may be delivered to a host cell non-specifically or specifically (i.e., to a designated subset of host cells) via a viral or non-viral means of delivery. Delivery methods of viral origin include viral particle-producing packaging cell lines as transfection recipients for the vector of the present invention into which viral packaging signals have been engineered, such as those of adenovirus, herpes viruses and papovaviruses. Non-viral based gene delivery means and methods may also be used in the invention and include direct naked nucleic acid injection, nucleic acid condensing peptides and non-peptides, cationic liposomes and encapsulation in liposomes, bacterial cells, and the like.

Methods of Treatment

In one embodiment the present invention provides a method of treating a subject by administering ChrR polypeptide or polynucleotide and a prodrug. In general, the methods of the invention reduce or inhibit growth of cancer cells by killing or decreasing the viability of the cells. As such, upon conversion of a prodrug to active drug, the viability of the cancer cell is reduced or inhibited. As used herein, the term "decreasing the viability," when used in reference to the effect of a active drug on a target cell, means that the population of target cells has fewer viable cells than a corresponding cell population that has not been exposed to the active drug. As such, the term "decreasing the viability" encompasses, for example, cells that are rendered incapable of mitosis, where the corresponding normal cells typically traverse the cell cycle; cells that are rendered defective in a metabolic pathway, where the pathway is typically active in corresponding normal cells; cells in which a pathway leading to cell death such as an apoptotic pathway has been induced, where the pathway is inactive in corresponding normal cells; and the like.

A method of reducing or inhibiting viability can be performed by contacting a cancer cell with an amount of a prodrug that, when converted to an active drug, is sufficient to decrease the viability of the cell. As used herein, the term "contacting," when used in reference to a prodrug and a cell, means that the prodrug is placed in sufficient proximity to the cell such that it can associate with the cell or a molecule expressed on the surface of the cell. As such, the term "contacting" has its commonly understood meaning, with the caveat that the prodrug need not be initially directly contacted with the cell, but can, for example, circulate to the cell through the vascular system, and the like.

The cell to be contacted with the prodrug can be any cancer cell and generally is a mammalian cancer cell, including a human cell such as a lymphocyte, a nerve cell, connective tissue cell, a muscle cell, an epithelial cell, a neuronal cell, a hepatocyte, and the like.

A method of the invention can be performed by administering the prodrug as a single treatment, either as a bolus injection or by infusion over a period of time, or can be performed as a series of separate treatments over a period of time, including days, weeks, or longer. An amount of a prodrug that, when converted to a active drug, is sufficient to allow the selective killing of cancer cells in a subject can be determined using the methods disclosed herein, and can further be optimized using routine clinical methods, including Phase I, II and III clinical trials. Efficacy of the method similarly can be determined using routine clinical methods, which, as discussed above, will depend in part on the nature of the cancer.

A prodrug generally is administered to an individual as a composition that includes a pharmaceutically acceptable carrier. Additionally, one can enhance the therapeutic efficacy of a second therapeutic by administering in conjunction with the methods of this invention. Administration can be prior to, subsequent to or concurrently with the other therapy.

The route of administration of a pharmaceutical composition containing the prodrug and ChrR will depend, in part, on the chemical structure of the compound. A pharmaceutical composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. Where the cancer is localized in the individual, for example, in the liver, kidney, lungs, or other organ, the pharmaceutical composition containing the prodrug can be administered to the site, for example, intravenously or intraarterially into a blood vessel supplying the tissue or organ, or by inhalation into the lungs. In prodrug therapy, the prodrug reducer is often administered first, there then follows a period of incubation to permit the reducing enzyme to localize at the site of the solid tumor and any free reductive enzyme to be cleared from the system. After this incubation period, the prodrug administered, so that it is selectively reduced at the tumor site.

The total amount of a prodrug to be administered in practicing a method of the invention can be administered to an individual as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary.

Pharmaceutical Compositions

ChrR polypeptides, nucleic acids encoding such polypeptides, and/or prodrugs described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of ChrR, prodrug (or its corresponding active drug) or nucleic acid of interest. Such methods comprise formulating a pharmaceutically acceptable carrier with an agent that modulates expression or activity of an active compound of interest. Such compositions can further include additional active agents. Thus, the invention further includes methods for preparing a pharmaceutical composition by formulating a pharmaceutically acceptable carrier with an agent that modulates expression or activity of ChrR (including expression vectors for expression of ChrR), prodrug (or its corresponding active drug) or nucleic acid of interest and one or more additional active compounds.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL.™.

(BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of ChrR (i.e., an effective dosage) is the amount of ChrR that is administered to a subject to produce a desired therapeutic effect in the subject. In the case of ChrR prodrug therapy applications, a therapeutically effective amount of the ChrR is an amount sufficient to convert enough prodrug to active drug that a symptom of the disorder being treated is ameliorated.

Typically, the amount of ChrR to be delivered to a subject will depend on a number of factors, including, for example, the route of administration, the activity of the ChrR, the degree to which it is specifically targeted to the desired cells, tissues or organs of the subject, the length of time required to clear the non-specifically bound ChrR from the subject, the desired therapeutic effect, the body mass of the subject, the age of the subject, the general health of the subject, the sex of the subject, the diet of the subject, the subject's immune response to the ChrR, other medications or treatments being administered to the subject, the severity of the disease and the previous or future anticipated course of treatment.

For applications in which a prodrug also is administered, other factors affecting the determination of a therapeutically effective dose will include, for example, the amount of prodrug administered, the activity of the prodrug and its corresponding active drug, and the side effects or toxicities of the prodrug and the active drug. In one embodiment, administration of ChrR is systemic. In another embodiment, administration of ChrR is at or near the target.

Typically a prodrug also is administered to the subject. It is understood that appropriate doses of prodrugs depend upon a number of factors within the ken of the ordinarily skilled physician, veterinarian, or researcher. Exemplary doses include milligram or microgram amounts of the prodrug per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a prodrug depend upon the potency of the prodrug with respect to the desired therapeutic effect. When one or more of these prodrugs is to be administered to an animal (e.g., a human), a physician, veterinarian, or researcher may, for example, prescribe a relatively low dose at first, subsequently increasing the dose until an appropriate response is obtained.

The timing of administration of the prodrug is another important factor to be considered. The ChrR may administered to the subject prior to the prodrug, concurrently, or following administration. In one embodiment, administration of the prodrug is systemic. In another embodiment, administration of the prodrug is at or near the target to be bound.

The methods of the combination may be combined with conventional chemotherapeutic, radiologic and/or surgical methods of treatment. Cytotoxic agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Antimetabolite agents include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other natural products include azathioprine; brequinar; alkaloids and synthetic or semi-synthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithromycin); anthracenediones, e.g. mitoxantrone; azirinopyrrolo indolediones, e.g. mitomycin; and the like. Other chemotherapeutic agents include metal complexes, e.g. cisplatin (cis-DDP), carboplatin, etc.; ureas, e.g. hydroxyurea; and hydrazines, e.g. N-methylhydrazine. Other anti-proliferative agents of interest include immunosuppressants, e.g. mycophenolic acid, thalidomide, desoxyspergualin, azasporine, leflunomide, mizoribine, azaspirane (SKF 105685), etc. The antineoplastic agents taxols (or taxanes) hyperstabilize polymerized microtubules, leading to mitotic arrest and cytotoxicity in proliferating cells. Taxanes (or taxols), such as paclitaxel, docetaxel, etc. are of interest. Also of interest are the microtubule stabilizing epothilones (see Bollag et al. (1995) Cancer Research, Vol 55, Issue 11 2325-2333, herein incorporated by reference with respect to teachings of the class, and use thereof of these chemotherapeutic agents), e.g. epothilone A and epothilone B. Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

The present invention relates to the killing of neoplastic cells by combining an enzyme in conjunction with a prodrug, which combination provides a synergistic benefit when compared to either of the single therapies.

Experimental

The E. coli enzyme, ChrR, is attractive as an activator of prodrugs. By applying directed evolution through the technique of error-prone PCR, the capacity of this enzyme to reduce chromate has been improved by over 200-fold. Based on the general characteristics of ChrR, it was tested and confirmed that this enzyme can also reduce CB 1954, and another prodrug, mitomycin C (MMC). Furthermore, improvement in chromate reductase activity of the evolved enzymes also led to improvement in their capacity to reduce the two prodrugs. Compared to the wild type YieF, the evolved enzymes exhibit >5-fold increased capacity to kill HeLa cells. It is also shown that this enzyme can be effectively delivered to tumor cells using an attenuated strain of Salmonella typhimurium (SL 7838). These bacteria target both the aerobic and anaerobic zones of tumors, and do not infect normal tissues.

Materials and Methods
Bacterial strains, plasmids, genes and primers. These are listed in Table 1.

TABLE 1

Bacterial strains, plasmids, genes and primers

Relevant characteristics strain

| | |
|---|---|
| E. coli BL21 | DE3 allowing over-expression of desired protein under IPTG inducible T7 promoter |
| S. typhimurium SL 7838 | Attenuated strain containing aroA and sopE gene deletions |

Plasmids

| | |
|---|---|
| pET28a⁺ | pET28a⁺ expressing the desirable gene (NdeI/BamHI) |
| pCGLS1 | Containing Luciferase gene allowing in-vivo imaging |
| pET28a⁺::yieF[a] | E. coli YieF (GenBank accession no. NC 000913.2) |
| pET28a⁺::nfsA[a] | E. coli NfsA (GenBank accession no. P17117) | primers

| | |
|---|---|
| Fyief[b] | 5'-CGCGGGGGCATATGTCTGAAAAATTGCAGG T-3' |
| Ryief[c] | 5'-TTTGGGATCCTTAGATCTTAACTCGCTGAA-3' |
| FA120N | 5'-GTATTGATTCAGACCAGCTCAATGGGCGTGATT GG-3' |
| RA120N | 5'-CCAATCACGCCCATTGAGCTGGTCTGAATCAAT AC-3' |
| FN128Y | 5'-TTGGCGGCGCGCGCTGTCAGTATCACCTGCGCC AGA-3' |
| RN128Y | 5'-TCTGGCGCAGGTGATACTGACAGCGCGCGCCGC CAAT-3' |
| FN160T | 5'-GTTGATCCGCAAACCGGAGAAGTGATTGA-3' |
| RN160T | 5'-ATCAATCACTTCTCCGGTTTGCGGATCAAC-3' |
| RL175G | 5'-TTAACTCGCTGAATAAACTCACCAAATGCGGTC AATTGCCCGGTCAGGTG-3' |

[a]Protein accession number in PubMed data base.
[b]Bold underlie Nde I restriction site.
[c]Bold underlie BamH I restriction site.

Human tumor cell lines. HeLa cells were used in most experiments. Freshly grown cells were grown in minimum essential medium (HeLa Spinners Modified-SIGMA) supplemented with 10% fetal calf serum (Gibco-BRL), 10 μg ml⁻¹ penicillin, 100 µg ml⁻¹ streptomycin, 0.292 g L⁻¹ L-glutamine and 10 mM Hepes buffer (pH, 7.6). Cells were routinely diluted to $10^5$ ml⁻¹ to keep a continuous viable and active culture. When adherent HeLa cells were used, they were grown in DMEM media (Gibco-BRL) containing the same supplements.

DNA techniques. Small-scale plasmid DNA isolation from *E. coli* was carried out by miniprep (QIAGEN Inc. CA). Plasmids were transformed into *E. coli* BL21 (DE3) cells (INVITROGEN Inc.), and used for protein production. DNA sequencing was conducted by SEQUETECH Corporation CA using appropriate primers (Table 1).

Error-prone PCR. The chrR gene (which encodes the enzyme ChrR; GenBank accession no. DQ989184) was used as template. Random mutations were introduced in this gene by error prone PCR according to Chen and Arnold employing GeneMorph® II Random Mutagenesis kit (STRATAGENE Corporation, CA) protocol. The forward and reverse chrR primers were used to amplify full length hybrid products (Table 1).

Screening for improved enzymes. As mentioned in the Introduction, the screening procedure used was aimed at identifying genes that encoded enzymes with superior chromate reductase activity. It was later discovered that several enzymes improved in chromate reductase activity also possessed superior prodrug reducing activity. Products generated through error-prone PCR were ligated into the pET28a⁺ plasmid, and transformed into *E. coli* BL21 (DE3). Recombinants were selected on plates containing kanamycin at 50 µg ml⁻¹. High throughput screening of 6,000 recombinants was performed by inoculating colonies into individual wells of 96-well microtiter plates, containing 200 µl LB medium and kanamycin. After growth to stationary phase (overnight incubation, final $A_{660}$, 1-1.5), 20 µl aliquots from each well were used to inoculate a second series of plates, using M9 minimal medium. Each well received the same initial inoculum density. The first set of plates was stored at −80° C. after addition of glycerol. Cells in the second inoculation series were allowed to grow to mid-exponential phase and then exposed to 0.5 mM isopropyl-β-D-thiogalactopyranoside (IPTG) to induce the recombinant gene expression. After appropriate incubation time, cells were lysed by 30 µl BugBuster™ (NOVAGEN Inc.) addition and centrifuged for 20 min at 3,000 g. 100 µl of the supernatant were mixed with additional 100 µl solution of the following composition: 500 µM of potassium chromate; 2 mM of NADH; 100 mM of Tris HCl (pH, 7) and ddH₂O. Cr(VI) reduction was then determined as previously described by Ackerley et al.

Protein purification. The most efficient enzymes with chromate reductase activity were purified on nickel columns, as previously described (Park et al. Appl Environ Microbiol 2000;66:1788-95), using inocula obtained from the frozen plates. Several of these were subsequently tested also for CB 1954 and MMC reductase activity as described in the viability determination section below.

Site directed mutagenesis. Appropriate primers (Table 1) were used for site directed mutagenesis. These were designed to create single codon mutations following the method of Kuipers et al. The modified PCR products were cloned into pET28a⁺ and transformed into *E. coli* BL21 (DE3). Verification of the desired mutations was made by sequencing.

Viability tests. As mentioned in the Results section, these involved two incubation periods, prodrug activation, followed by assay of the toxic moiety generated by determining the loss of HeLa cell viability. Prodrug reduction mixture contained: MMC or CB 1954 and the enzyme at specified concentrations; 50 µM NADPH; and HeLa Cells Modified minimum essential medium (see above) to a final volume of 0.5 ml. Following prodrug reduction at 37° C., 0.5 ml of fresh HeLa cells (~0.5-1×10⁵) were added. The duration of the prodrug reduction was 30 min in all experiments; the HeLa cell exposure periods were as specified in the text. After the latter incubation, 20 µl of the color reagent, CellTiter 96®AqueousOne (PROMEGA Inc) were added to 100 µl aliquots of the reaction mixture. Following an additional 1 h of incubation, $A_{490}$ was measured in a BioTek microplate S330 reader.

Cell survival assay, using SL 7838 to deliver the wild type or evolved enzymes. SL 7838 contains deletions in the aroA and sopE genes. This strain is non-pathogenic in immunocompetent mice, but can colonize and persist in solid tumors. The strain was transformed with appropriate plasmids to express the yief (now chrR), nfsA or theY6 (now chrR6)-encoding yieFY6 gene. It was also transformed with a vector containing the lux operon, expressing the bacterial luciferase (product of the luxR gene) and its substrate. HeLa cells stably transfected to express firefly luciferase were added to black walled 96-well plates at a density of 1000 cells well⁻¹. Once the cells had attached, a dilution series of non-transformed SL 7838 or SL 7838 transformed with plasmids expressing the appropriate genes (Table 1) was added to the plates; 0.5 mM IPTG was added to induce the genes on the plasmids. After 1 h incubation, 15 µM CB 1954 was added. Light output per well produced from bacterial luciferase (no additional substrate added) or bacterial and firefly luciferase (following addition of 2 µl of 30 mg ml⁻¹ luciferin per well) was measured on an IVIS50 system (Xenogen Corp.). Percentage HeLa cell survival was determined by calculating firefly luciferase expression (total light output—bacterial light output) relative to wells containing unchallenged HeLa cells or HeLa cells treated with 70% ethanol. All experiments were performed at least in triplicate; error bars in the figures are SEM.

Computer Programs. Homology searches for enzymes were performed using blastp. Sequences were aligned with Clustal W.

Results

Prodrug activation by wild type YieF and the evolved enzymes. The loss of viability of HeLa cells was used to determine the capacity of different enzymes to activate the prodrugs, MMC and CB 1954. The experiments involved two incubation periods. In the first period, the enzyme and the drug were incubated to generate the toxic species; in the second period, which was initiated with the addition of HeLa cells to the reaction mixture, the extent of drug activation was inferred from the loss of HeLa cell viability. In the experiments described in this section, both the prodrug reduction and the subsequent cell exposure periods were of 30 min duration, and the enzyme and drug concentrations were 50 µg ml⁻¹ and 15 µM, respectively. HeLa cell survival was compared between reaction mixtures containing the WT *E. coli* YieF (now ChrR) in the presence of MMC or CB 1954, and controls from which the drug, the enzyme, or both were excluded. YieF (now ChrR)/MMC and YieF (now ChrR)/CB 1954 were both 30-40% more effective than the controls in reducing the viability of the HeLa cells (FIG. 1). This is the first demonstration that YieF has prodrug reducing activity. We also tested NfsA in this system; its effects were comparable to YieF (now ChrR), with either of the drugs (FIG. 1). Given this, and the fact that NfsA prodrug reduction is well characterized, the data presented below will compare the activity of our evolved enzymes to that of the wild type NfsA.

The above experiments were also conducted using a single incubation period in which HeLa cells were added at the same time as the drug and the enzyme. Very similar results were obtained, suggesting that the cytotoxic reduction products of the prodrugs were stable. Subsequent experiments utilized the two incubation method.

Error-prone PCR was carried out using the *E. coli* yieF (now chrR) gene and the evolved genes were screened for improved chromate reductase activity as described in Materials and Methods. Selected enzymes showing superior chromate reductase activity were also tested for prodrug reduction. Two of these enzymes, Y3 (now ChrR3) and Y6 (now ChrR6), exhibited improved activity for prodrug reduction, with Y6 (now ChrR6), the more active of the two, showing some 90% greater reduction in HeLa cells survival compared to the controls (FIG. 1).

Figure 2:
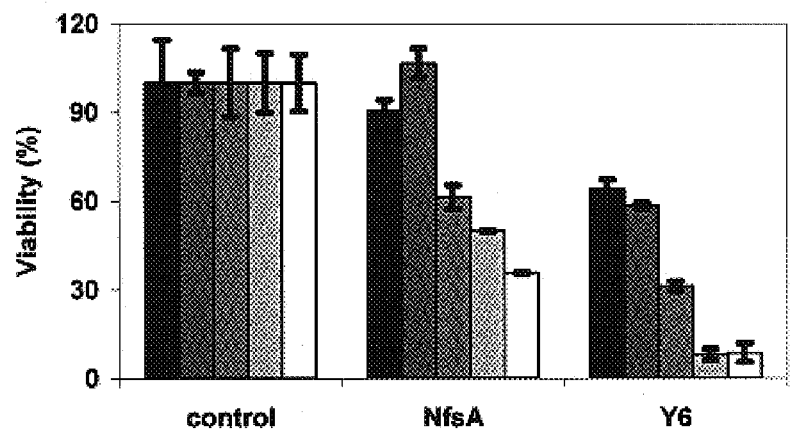
FIGS. 2A-2B. The effect of different MMC (A) or CB 1954 (B) concentrations on the viability inhibition of HeLa cells in the presence of the wild type or the evolved enzyme (50 µg ml$^-$). The drug concentrations were: 1 µM, (■); 3 µM, (■); 5 M, (■); 10 µM, (■); or 30 µM, (□).
Figure 2:
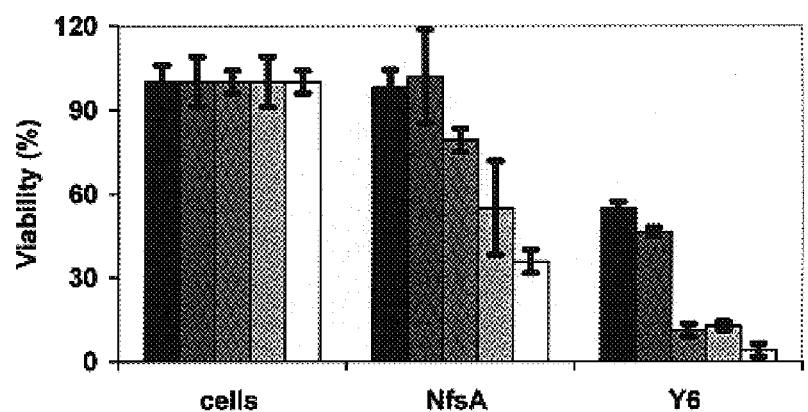
Figure 3:
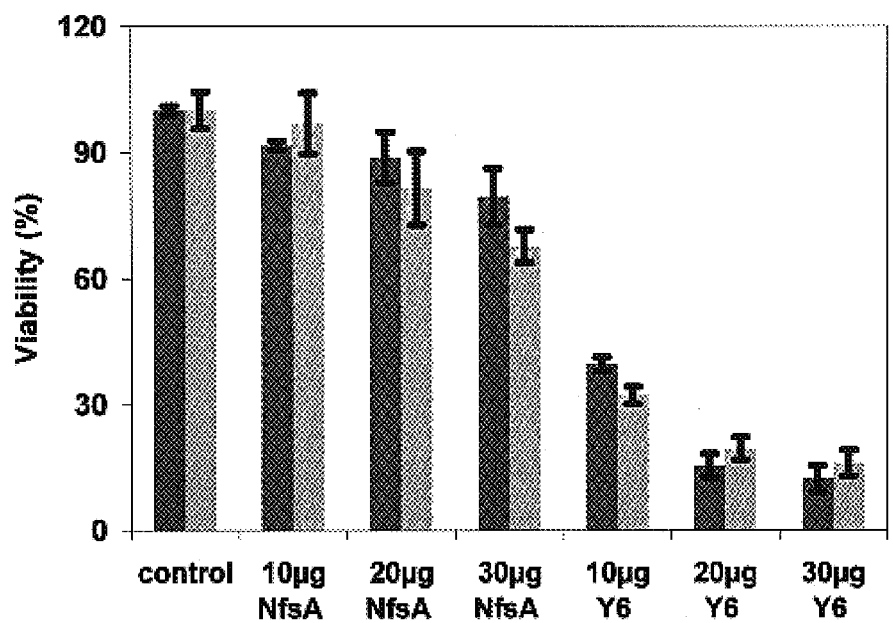
FIG. 3. The effect of different NfsA or Y6 (now called ChrR6) enzyme concentrations on the viability of HeLa cells in the presence of 15 µM MMC (■) or CB 1954 (■).
Figure 4A:
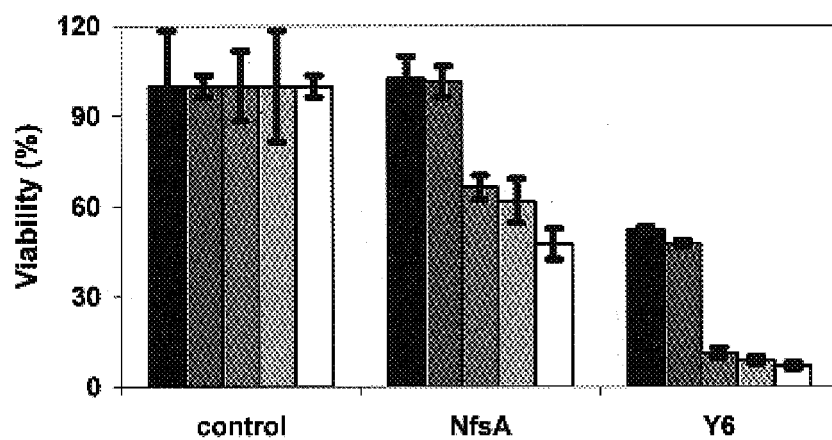
Figure 4A:
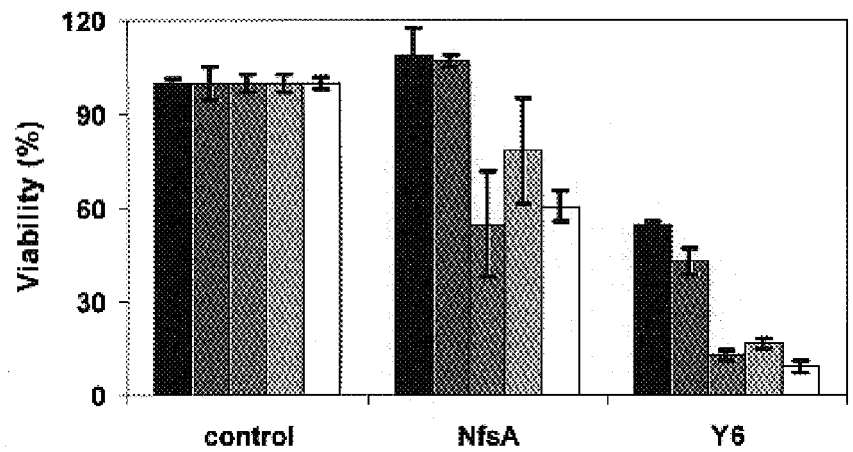

Effect of changing experimental parameters. To test that the results reported above were not confined to the conditions used, the effect of changing drug or enzyme concentration, or the duration of HeLa cells exposure period, were investigated. Neither of the drugs produced much killing of the HeLa cells at a concentration of 1 or 3 μM when NfsA was used as the activating enzyme (FIG. 2). However, at these drug concentrations, Y6 (now ChrR6) gave a 30-40% reduction in viability. At 5 and 10 μM, both drugs produced appreciable cell killing with NfsA, but this was still markedly less than that generated by Y6 (now ChrR6). Increasing NfsA concentration from 10-30 μg ml$^{-1}$ increased the killing of HeLa cells from around 5% to 25% (FIG. 3). In contrast, killing by Y6 (now ChrR6) in this enzyme concentration range was between ca. 70% to around 90%. The effect of varying the cells exposure period gave similar results. With either of the prodrugs present, NfsA caused little or no reduction in cell viability during the first 20 min of incubation (FIG. 4). Y6 (now ChrR6) enzyme, however, generated some 40% reduction in this period. With further incubation of up to 180 min, while NfsA produced up to 50% reduction, Y6 generated up to 90% reduction of HeLa cell viability, showing that during this prodrug incubation period, Y6 (now ChrR6) was able to generate more of the activated drug than NfsA. The fact that increasing incubation times generated progressively greater killing of HeLa cells is consistent with the stability of the cytotoxic reduction products, as noted above.

Figure 5:
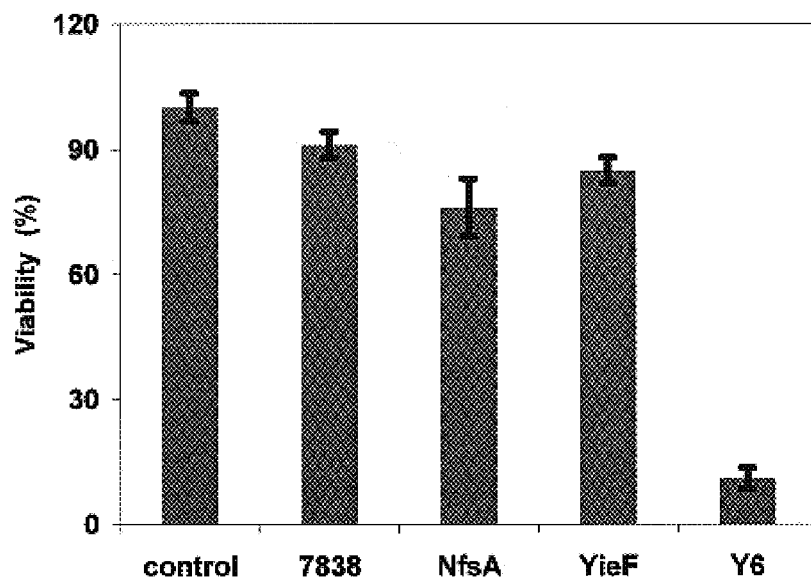
FIG. 5. Viability of HeLa cells after exposure to 15 µM CB 1954 alone (control); CB 1954 and untransformed SL 7838; or CB 1954 and SL 7838 expressing NfsA, YieF (now called ChrR) or Y6 (now called ChrR6).

SL 7838 as a delivery vehicle to tumor cells. For Y6 (now ChrR6) to be effective in cancer therapy, it is necessary to find a means of targeting it to the tumor cells. We tested the *S. typhimurium* strain 7838 (SL 7838), transformed with different plasmids (see Methods), as a potential vehicle to attain this objective. IPTG was used to induce the wild type and mutant enzymes encoded by the plasmids. In these experiments, the prodrugs were activated by bacteria producing the specified enzymes instead of, as in previous experiments, the added enzymes. Only CB 1954 was used because MMC was toxic to SL 7838 at even low concentrations (5 μM). In the presence of CB 1954, SL 7838 bacteria alone produced 10%; those expressing WT NfsA or YieF (now ChrR), 10-25%; while bacteria expressing Y6 (now ChrR6), produced 90% reduction in survival of HeLa cells (FIG. 5). This is consistent with the data presented above for the superiority of Y6 (now ChrR6) over the WT enzymes, and demonstrates that SL 7838 can be used as an effective delivery vehicle.

Figure 6:
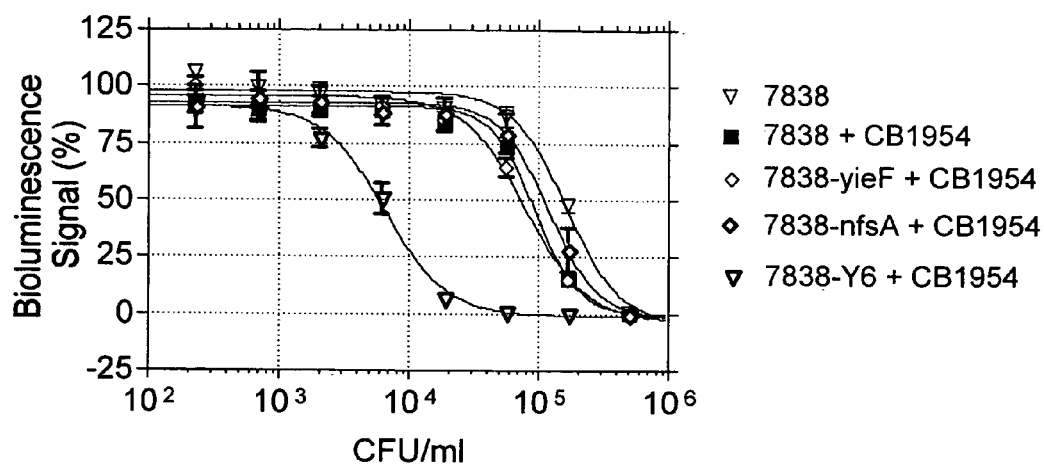
FIG. 6. The use of SL 7838 to deliver wild type or evolved enzymes to adherent HeLa cells. Survival of HeLa-luc cells was measured via light output after addition of luciferin (see Methods). Data are presented as percentage luminescent signal relative to control wells containing luc-transfected HeLa cells only (100%), or following treatment with 70% ethanol (0%). All points are averages of three replicates. CB 1954 concentration was 15 µM.

Further analysis was performed to test the efficiency of SL 7838 to deliver the enzymes to surface-adhered HeLa cells. Firefly luciferase-expressing HeLa cells were incubated with different CFU/ml of the various SL 7838 strains for 1 h before addition of CB 1954 and in situ production of toxic products. After a further 3 h incubation period the firefly luciferase substrate (luciferin) was added, and the light output was used to quantify HeLa cell survival (FIG. 6). It was found that CB 1954 did not inhibit replication of SL7838 and that neither expression of WT or evolved enzyme reduced the replication capacity of the bacteria. SL 7838 expressing Y6 (now ChrR6) enzyme required at least an order of magnitude less bacteria for effective HeLa cell killing than cells expressing the wild type enzymes, YieF (now ChrR) or NfsA. In fact the killing by the latter was scarcely greater than seen in controls, using untransformed bacteria with or without CB 1954.

Amino acid sequence of the Y6 (now ChrR6) enzyme. Four substitutions were found in Y6 protein: V120A, Y128N, T160N and Q175L. When each altered amino acid was individually reverted to its original residue (see Materials and Methods), only the N128 to Y reversion diminished Y6 (now ChrR6) activity (Table 2).

TABLE 2

Killing of HeLa cells by Y6 (now ChrR6) reversion enzymes. HeLa cells were incubated in the presence of 15 μM of one of the prodrugs, and 50 μg ml$^{-1}$ of the enzyme.

| Variant | MMC Viability (%) | CB 1954 Viability (%) |
|---|---|---|
| Cells | 100 ± 8 | 100 ± 5 |
| YieF | 65 ± 9 | 72 ± 2 |
| Y6 | 26 ± 3 | 7 ± 3 |
| A120V | 24 ± 4 | 4 ± 5 |
| N128Y | 95 ± 3 | 102 ± 8 |
| N160T | 30 ± 9 | 12 ± 2 |
| L175Q | 26 ± 2 | 9 ± 4 |

EXAMPLE 2

Figure 7:
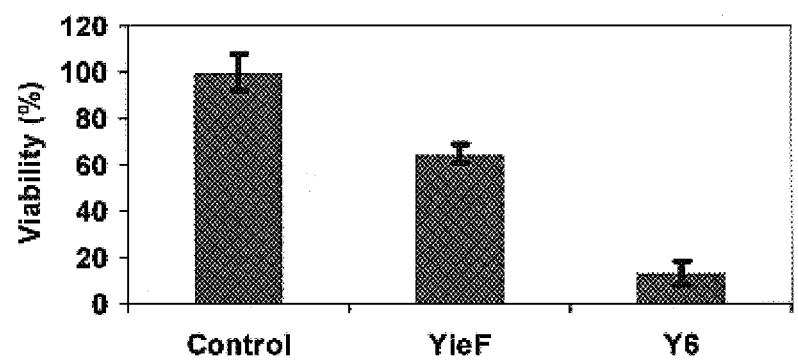
FIG. 7. CNOB killing effect of the wild type YieF (now called ChrR) compared with Y6 (now called ChrR6) on pure protein basis.

A Novel Prodrug for Reductive Cancer Chemotherapy that can be Visualized In-Vivo and can be used in High Throughput Screening Assays for the Development of Improved Nitro-Reductase Proteins for Prodrug Activation In Vivo Use of 6-chloro-9-nitro-5-oxo-5H-benzo[a]phenoxazine (CNOB) as prodrug and for following in vivo activation of prodrugs. A variety of enzymes are capable of reducing prodrugs to their toxic forms (Denny, 2003 New Zealand J. of Boimed and Biotech 1:48-70; Knox and Chen, 2004 Methods Enzymol. 382:194-221). We recently showed that the *E. coli* NAD(P)H oxidoreductase YieF (now ChrR) (product of the yieF gene) can reduce CB 1954 to its cytotoxic form and can be used for reductive prodrug chemotherapy (Barak et al, 2006 Mol. Cancer Ther. 5:97-103). Surprisingly, while testing CNOB reduction by YieF (now ChrR) and other nitroreductase (NfsA; See Barak et al, 2006) in the presence of cancerous cells, we found that there was significant increase of cell killing compared to the control. Viability loss of HeLa cancer cells was used to determine the capacity of YieF (now ChrR) to activate CNOB (FIG. 7). Furthermore, our improved YieF (now ChrR)-based mutant enzyme, Y6 (now ChrR6), was more active in promoting HeLa cell killing by CNOB compared to the wild type enzyme YieF (now ChrR) (FIG. 7).

The product of CNOB reduction is fluorescent, and since its fluorescence emission is at >600 nm wavelength, it is suitable for in situ imaging. We have demonstrated this using HeLa cells and bacteria SL 7838 expressing both GFP and the prodrug converting enzyme, Y6 (now ChrR6).

Figure 8:
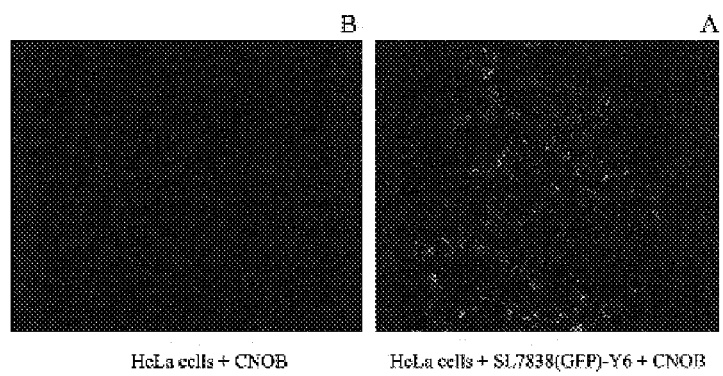
FIGS. 8A-8B. Confocal imaging of HeLa cells reduction of CNOB in the absence (A) or presence (B) of infection by GFP and Y6 (now called ChrR6)-expressing SL 7838.

In FIG. 8, it can be seen that CNOB is converted to fluorescent product (red) in HeLa cells infected with the bacteria (green), and that the red fluorescence can be seen also in uninfected cells indicating effective bystander effect. Thus, CNOB can be used both as a prodrug and as an agent to image its own conversion to toxic (and fluorescent) product. Also, since CNOB is a competitive inhibitor of CB 1954, it can be used to visualize the trafficking also of the latter prodrug, and possibly that of other nitro-prodrugs.

Figure 9:
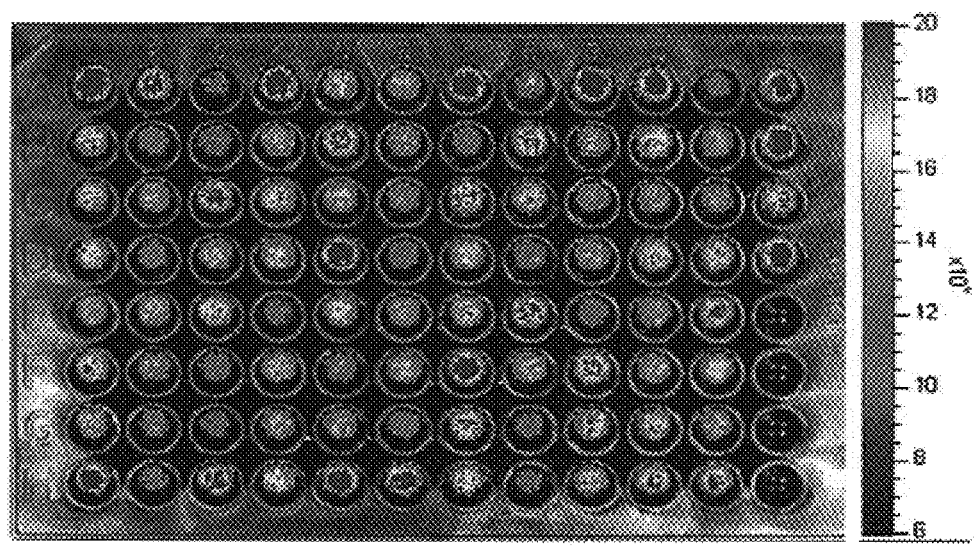
FIG. 9. High throughput screening of mutants for CNOB reduction. Wells E-H, 12 are controls that exhibit no fluorescence.

In FIG. 9, it is clearly demonstrated that reduced CNOB can be tracked directly in blood samples taken from the subjects and can be monitored easily in a fluorometer. Thus, CNOB can be used as a diagnostic molecule to assess drug concentration directly in patients. This will permit determination of the extent of drug conversion and optimal drug dose.

Use of CNOB in high throughput screening. No satisfactory rapid method for detecting nitro-prodrug reduction is available that could be used in high throughput screening of enzyme libraries for isolating improved mutant enzymes. We have now developed such a method based on the use of CNOB, as in its native state, it is non-fluorescent, but upon reduction, generates a fluorescent compound which absorbs and emits light of 570 and 630 nm wavelength, respectively, reduction of CNOB generates a highly fluorescent compound (aminophenoxazine) and thus permits rapid screening (FIG. 9).

We have already isolated improved mutant enzymes for CNOB reduction using this screening technique. To evaluate if CNOB competes with CB 1954 on the active site of the enzyme we performed a competition assay. CNOB and CB 1954 proved to be competitive inhibitors of each other implying that they occupy the same active site of the enzyme. This also suggests that the use of CNOB with these enzymes will make it possible to carry out dynamic characterization in vivo also of CB 1954 (and very likely other nitro-prodrugs).

Figure 10:
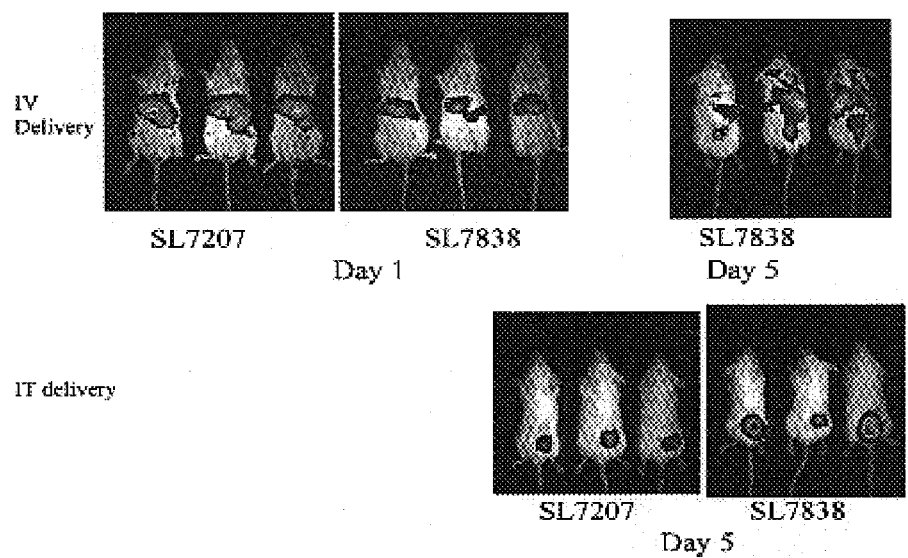
FIG. 10. In vivo visualization of SL 7838 and SL 7207 intra tumor colonization over time using either IV or IT cells delivery. 5e$^5$ bacterial Cells were delivered in each treatment.

Effectiveness of CNOB, as of any prodrug, in cancer therapy depends on specific targeting of nitroreductases to the tumor cells. It was previously shown that a *Salmonella typhimurium* strain 7838 (SL 7838) could serve as a carrier vehicle of the appropriate genes in vivo (FIG. 10). However, a variety of other delivery vehicles (e.g. bacterial, cellular, viral or liposomal) could serve to deliver YieF (now ChrR), Y6 (now ChrR6) or similar genes to the tumor.

Figure 11:
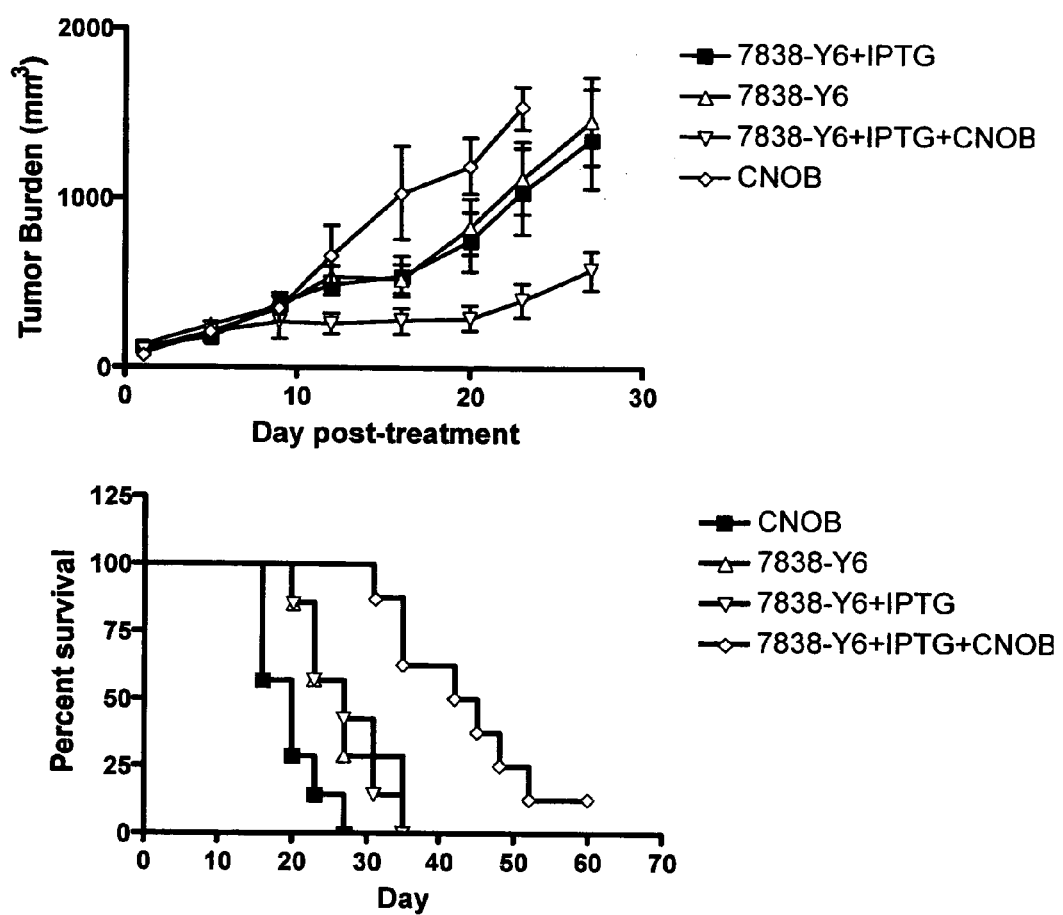
FIG. 11. In vivo efficacy assays of mice treated with CNOB at concentration of 15 µM following IT inoculation and colonization of SL7838 overexpressing ChrR6. A) In vivo efficacy assays of mice treated with CNOB at concentration of 15 µM following IT inoculation and colonization of SL7838 overexpressing ChrR6. A) survival curve of JC tumor bearing bulb C mice, which were infected with 10$^5$ SL7838, followed by IT CNOB administration at a concentration of 15 µM. CNOB, (Δ); SL7838::chrR6, (■); SL7838::chrR6+IPTG, (∇); and SL7838::chrR6+IPTG+CNOB, (◇); and B) tumor burden as measured by it's volume.

FIG. 11 shows the In vivo efficacy of mice treated with CNOB at concentration of 15 µM following IT inoculation and colonization of SL7838 overexpressing ChrR6.

It is understood that the examples and embodiments described herein are for illustrative purposes only and that various modifications or changes in light thereof will be suggested to persons skilled in the art and are to be included within the spirit and purview of this application and scope of the appended claims.

---

What is claimed is:

1. A method for treating cancer, the method comprising: administering to an individual in need thereof, an effective amount of: a) at least one vector, which comprises an isolated polynucleotide encoding a bacterial chromium reductase (ChrR) enzyme capable of converting a prodrug into an active cytotoxic compound, expression of the enzyme being controlled by an operably-linked promoter; and b) a prodrug capable of being converted into an active cytotoxic compound by said ChrR enzyme, wherein said at least one vector is administered by intratumoral inoculation or injection.

2. The method according to claim 1, wherein said ChrR enzyme is an *E. coli* enzyme.

3. The method according to claim 1, wherein said ChrR enzyme comprises at least one amino acid substitution relative to the wild-type *E. coli* enzyme.

4. A method for treating cancer, the method comprising: administering to an individual in need thereof, an effective amount of: a) at least one vector, which comprises an isolated polynucleotide encoding *E. coil* chromium reductase (ChrR) enzyme comprising an amino acid other than tyrosine at position 128 and capable of converting a prodrug into an active cytotoxic compound, expression of the enzyme being controlled by an operably-linked promoter; and b) a prodrug capable of being converted into an active cytotoxic compound by said ChrR enzyme, wherein said at least one vector is administered by intratumoral inoculation or injection.

5. The method according to claims 4, wherein said prodrug is in the dinitrobenzamide class.

6. The method according to claim 5, wherein said prodrug is 5-aziridinyl-2,4-dinitrobenzamide (CB 1954) or mitomycin C.

7. The method according to claim 4, wherein said vector is a plasmid vector.

8. The method according to claim 4, wherein said vector is provided in a transfected bacterial cell.

9. A method for treating cancer, the method comprising: administering to an individual in need thereof, an effective amount of: a) a plasmid vector, which comprises an isolated polynucleotide encoding *E. coil* chromium reductase (ChrR) enzyme comprising an amino acid other than tyrosine at position 128, expression of the enzyme being controlled by an operably-linked promoter and provided in a transfected attenuated *Salmonella typhimurium*; and b) a prodrug selected from 5-aziridinyl-2,4-dinitrobenzamide (CB1954) and mitomycin C, wherein said transfected attenuated *Salmonella typhimurium* is administered by intratumoral inoculation.

10. A kit for treatment of cancer comprising: a) a plasmid vector, which comprises an isolated polynucleotide encoding *E. coil* chromium reductase (ChrR) enzyme comprising an amino acid other than tyrosine at position 128, expression of the enzyme being controlled by an operably-linked promoter, in a pharmaceutically acceptable carrier, excipient, diluent, or buffer; and b) a prodrug selected from 5-aziridinyl-2,4-dinitrobenzamide (CB 1954) and mitomycin C, in a pharmaceutically acceptable carrier, excipient, diluents, or buffer.

11. The kit of claim 10, wherein the isolated polynucleotide encodes *E. coil* ChrR polypeptide, wherein said polypeptide comprises a glutamine or asparagine at position 128.

* * * * *